United States Patent [19]
Chekroun

[11] 3,986,031
[45] Oct. 12, 1976

[54] SCANNING DEVICE FOR AXIAL TRANSVERSE TOMOGRAPHY

[75] Inventor: Rene Chekroun, Paris, France

[73] Assignee: Compagnie Generale de Radiologie, Paris, France

[22] Filed: Sept. 26, 1975

[21] Appl. No.: 617,080

[30] Foreign Application Priority Data
Oct. 14, 1974  France .............................. 74.34490

[52] U.S. Cl. ............................. 250/360; 250/445 T
[51] Int. Cl.[2] ................. G01N 23/00; G01N 23/02; G01N 23/04
[58] Field of Search ................ 250/445 T, 360, 363, 250/439

[56] References Cited
UNITED STATES PATENTS
3,924,131   12/1975   Hounsfield ........................ 250/360

Primary Examiner—Alfred E. Smith
Assistant Examiner—T. N. Grigsby
Attorney, Agent, or Firm—Brady, O'Boyle & Gates

[57] ABSTRACT

A scanning device for axial transverse tomography comprising a single motor mounted on a first mobile support, which is rotatably mounted on a fixed base, and coupled, on the one hand, to a first indexing mechanism driving a sprocket or pinion, which engages with geared structure or chain secured to the fixed base in order to intermittently rotate the first support about a horizontal axis and, on the other hand, to a second mechanism converting a continuous rotational motion into a rectilinear reciprocating motion of a second mobile support relative to the first one, and which carries the X-ray source and detector assembly.

11 Claims, 6 Drawing Figures

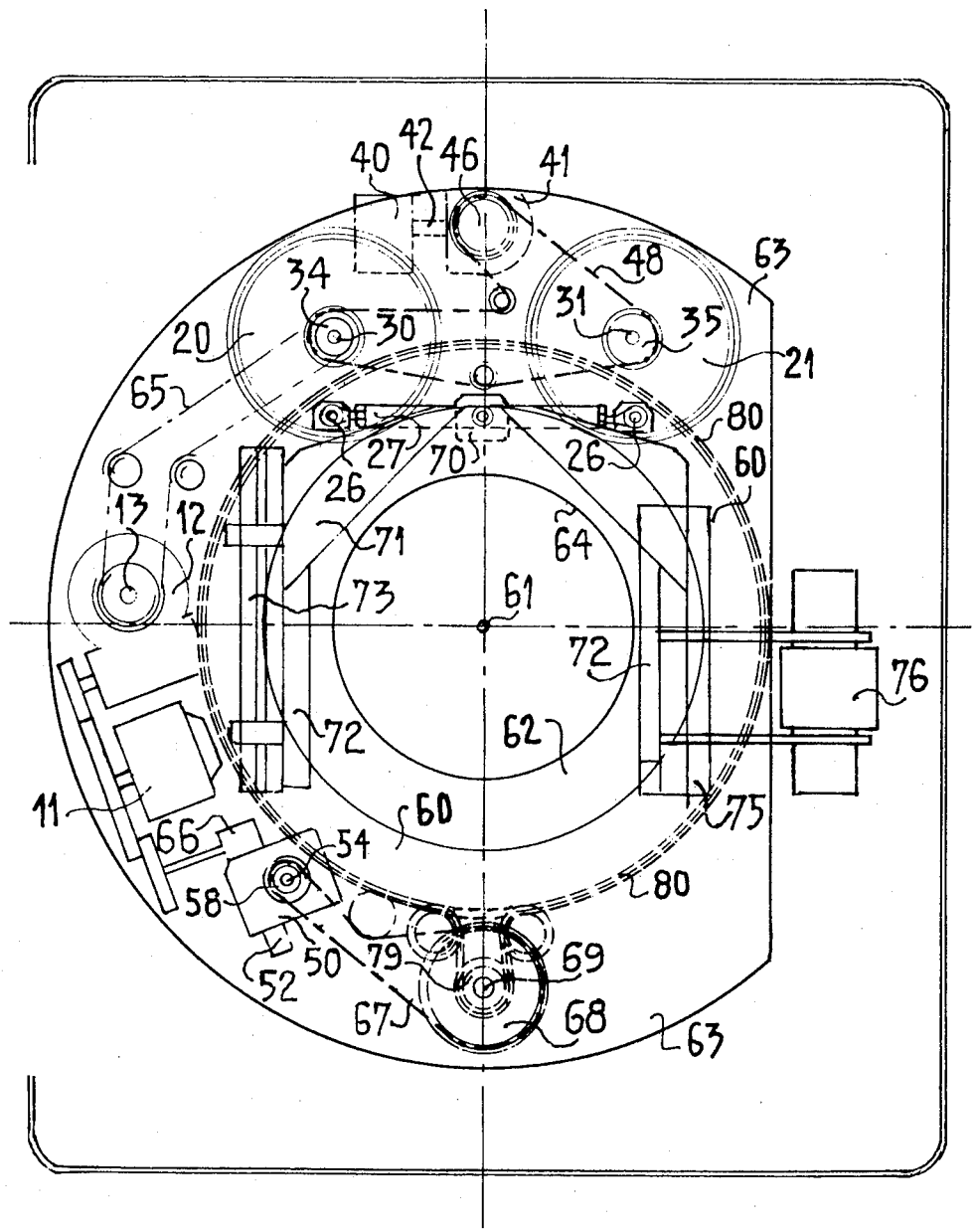

SCANNING DEVICE FOR AXIAL TRANSVERSE TOMOGRAPHY

The present invention relates to a scanning device for axial transverse tomography, wherein to an assembly comprising a source and a detector respectively producing and detecting penetrative radiation is imparted, on the one hand, a rectilinear reciprocating motion perpendicular to the axis of the radiation beam, and on the other hand, at each reversal of said rectilinear motion, a pivoting motion of given magnitude about an axis perpendicular both to the axis of the beam and to the direction of rectilinear motion, in order to perform transverse tomography sections in one or more planes parallel to that of the axis of the moving beam and perpendicular to the axis of pivot.

A method of and an apparatus for performing axial transverse tomography operations of this kind have been described, for example, in British patent specification No. 1,283,915. FIG. 3 of this patent, similar to FIG. 1 of the accompanying drawing, illustrates the scanning of an object which is to be examined by means of a penetrative radiation, such as for example X-rays or gamma rays, using an assembly constituted by a source emitting a narrow parallel beam of said radiation and a detector arranged in such a manner as to receive the radiation after it has passed through the object, the detector furnishing, for example, an electrical signal of amplitude proportional to the intensity of the incident radiation, in order to make it possible to measure the absorption of said radiation by the object. The source and the detector are here imparted rectilinear and simultaneous motions perpendicular to the beam axis and, at the end of each travel of this rectilinear motion, are imparted an intermittent and simultaneous pivoting or rotary motion about an axis perpendicular to the plane in which the beam axis is moving, in order to carry out another rectilinear motion at a different angle of incidence.

In one known scanning device of this kind, the simultaneous rectilinear motions of source and detector, are produced by means of two identical threaded shafts engaging with respective nuts integral with the source and the detector and driven in the same direction by a single motor or by two controlled motors, the rotary motion being produced by means of a stepping motor driving a gearing arrangement which engages with a geared ring, the motor or the ring being integral with a support, which carries the source-detector assembly and its control mechanism in a pivotable fashion. The rectilinear motion may be linear, that is to say of constant speed kind, or may be a stepping motion whilst its control, its reversal and its synchronising with the rotative motion, are performed with the help of relatively complex electronic means.

The object of the present invention is a simplified scanning device of this kind, in which the production of the rectilinear motion and of the rotation controlled is by means of a single motor and in which the synchronization of these motions is performed by means of transmissions and a mechanism called indexing means such as the "Maltese cross" type.

It is an object of the present invention, to provide a scanning device for axial transverse tomography comprising a first mechanism converting the continuous rotary motion of a motor into a rectilinear reciprocating motion of a first movable support carrying at least one X-ray source and at least one detector per source, respectively arranged at either side of the object to be examined, and a second mechanism converting said continuous rotary motion of said same motor into an intermittent pivoting motion of a second movable support which carries the first support and which is displaced relatively to a fixed base, at the time of reversal of the direction of the rectilinear motion.

The invention will be better understood and its features and advantages become apparent, from the following description, given by way of example, and the accompanying drawings in which:

FIG. 1 illustrates the diagram of the scanning motion executed by the assembly of source and detector, in order to perform axial transverse tomography operations;

FIG. 2 schematically illustrates the mechanism for carrying out the rectilinear scanning of the present invention;

FIG. 5 illustrates a front elevational view of simplified form, of a device in accordance with the invention.

Figure 1:
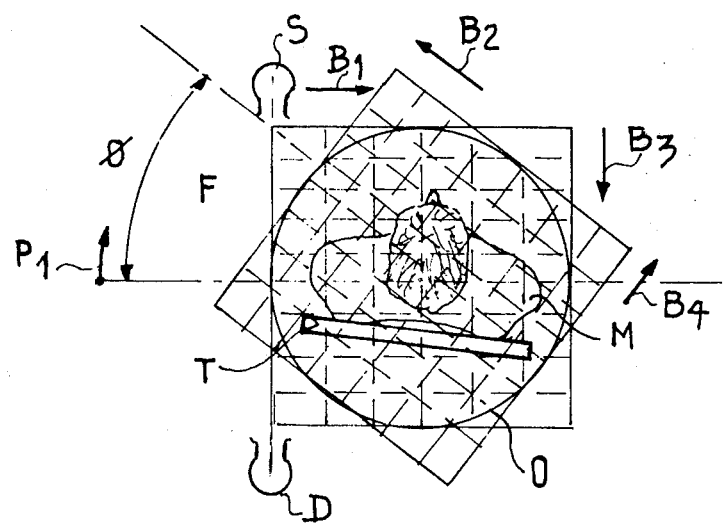

In FIG. 1, the reference M signifies a patient lying upon an examination table T. The table T can move in the direction of its own longitudinal axis and passes through a central opening O formed in the structure (not shown) designed to carry and displace the assembly constituted by an X-ray source S emitting a collimated X-ray beam designated by F and illustrated by dashed lines, and a radiation detector D arranged in order to receive the beam after it has passed through the space separating the source S and the detector D, in which the patient M is located.

The simultaneous displacements of the assembly of source S and detector D, are composed, as referred to earlier, of a rectilinear motion perpendicular to the beam F and indicated by the arrows B1 to B4, and, at the end of each rectilinear scan, as for example in the direction B1, a pivoting motion P1 through an angle $\phi$ about an axis of rotation perpendicular to the beam F as well as to the plane in which the latter is displaced, this axis of pivoting coinciding in the present instance with the axis of the circular opening O.

After this pivoting motion P1, a new rectilinear motion in the direction indicated by the arrow B2, takes place, and so on. The rectilinear motions are produced by means of a scanning mechanism (not shown) assembled on the mobile part of the supporting structure containing the opening O. This mobile part is assembled on a fixed part to which it is attached in such a manner as to be able to rotate about an axis of rotation by means of a so-called indexing mechanism which makes it possible to pivot the mobile part in an intermittent manner, synchronously with the reversals of the rectilinear scan.

The output signals from the detector D, whose amplitudes are functions of the degree of transmission or absorption of the radiation passing through the object being examined, in different positions and at different angles, are stored in a memory, and, at the end of the scanning process, subjected to a computing operation which makes it possible to create a map of the X-ray transmission or absorption by different elements of a fictitious matrix located in the plane of the beam F, that is to say in a plane of section or tomography plane perpendicular to the axis of the intermittent rotation.

Figure 2:
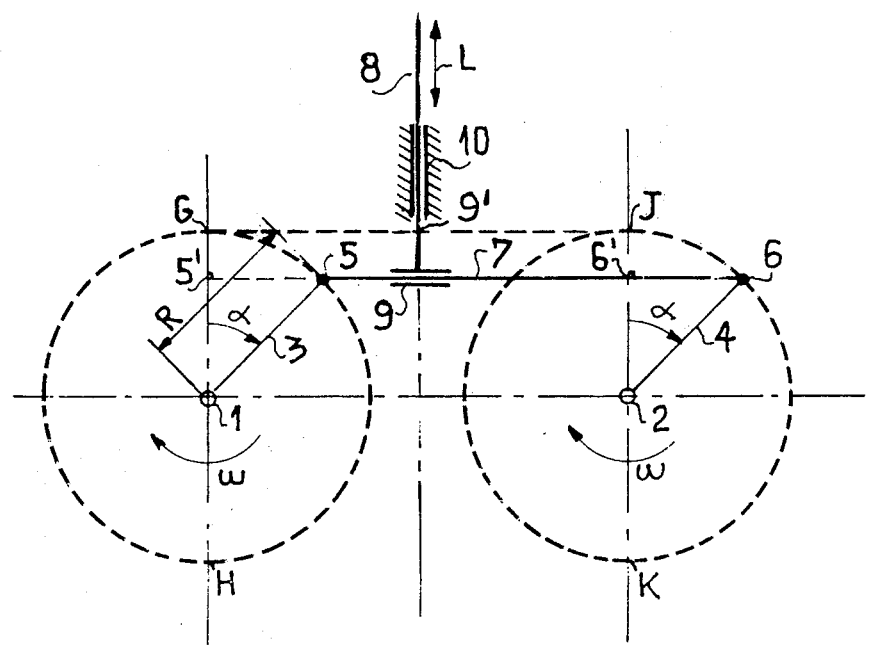

FIG. 2 illustrates the principle of the scanning mechanism which makes it possible to obtain the rectilinear reciprocating motion.

This mechanism comprises two parallel shafts 1 and 2 each with a crank 3, 4 having a length of R. These two cranks are connected together by a straight coupling link 7 respectively articulated to the free ends 5 and 6 of the cranks 3 and 4. The length of the link 7 is equal to the centre-to-centre interval between the shafts 1 and 2, which should be greater than 2R. A straight rod 8 is connected to a link 7 by means of a first sleeve 9 which can slide along the link 7. A second fixed sleeve 10 guides the rod 8 linearly in the direction of the double arrow L, perpendicular to the link 7.

When the two shafts 1 and 2 perform a rotary motion of angular velocity $\omega$, the points 5 and 6 describe circles of radius R and the rod 8, guided by the sleeve 10, will describe a rectilinear axial motion.

The motion of any point on the rod 8 is identical to that of the point 5' which is the projection of the point 5 on to the diameter GH parallel to the rod 8, or to that of the point 6' which is the projection of the point 6 on to the diameter JK parallel to the rod 8.

If we take as time origin the instant at which 5 is at G and 6 is at J (the sleeve 9 is then at 9'), then, at the instant $t$, a displacement G5' or J6' equal to $R - R \cos \alpha = R (1 - \cos \alpha)$ will be obtained. If we designate the distance covered by the sleeve 9 or by the rod 8 during the time $t$, by E ($t$), then we obtain E ($t$) = R (1 $-$ cos $\alpha$). However, if the shafts are rotating synchronously at the angular velocity $\omega$, then we have $\alpha = \omega t$. The equation for the distances travelled by the rod 8 as a function of time, is thus E ($t$) = R (1 $-$ cos $\omega t$).

This is the equation of a sinusoidal function characterised by a periodicity T = $2\pi/\omega$ which is the time of a complete rotation of the shafts 1 and 2, and by a peak-to-peak amplitude of $E_{max}$ = 2R (0 ≤ E ≤ 2R).

The rod 8 is thus imparted a rectilinear reciprocating motion of amplitude 2R.

During one half cycle T/2 = $\pi/\omega$, a rectilinear motion in one direction (2R) takes place and during the next half cycle ($\pi/\omega$), a rectilinear motion (2R) in the opposite direction.

The equation of the rectilinear motion E ($t$) = R (1 $-$ cos $\omega t$) shown that the amplitude of the motion is proportional to R (the lengths of the cranks 3 and 4).

To vary the amplitude of the linear motion, it is therefore merely necessary to simultaneously vary the lengths R of the cranks 3 and 4, only the amplitude of the motion changing while its period remains the same if the angular velocity $\omega$ remains constant (T = $2\pi/\omega$). Thus, for all possible values of R, a rectilinear reciprocating motion which is a sinusoidal function of time, is obtained.

Figure 3:
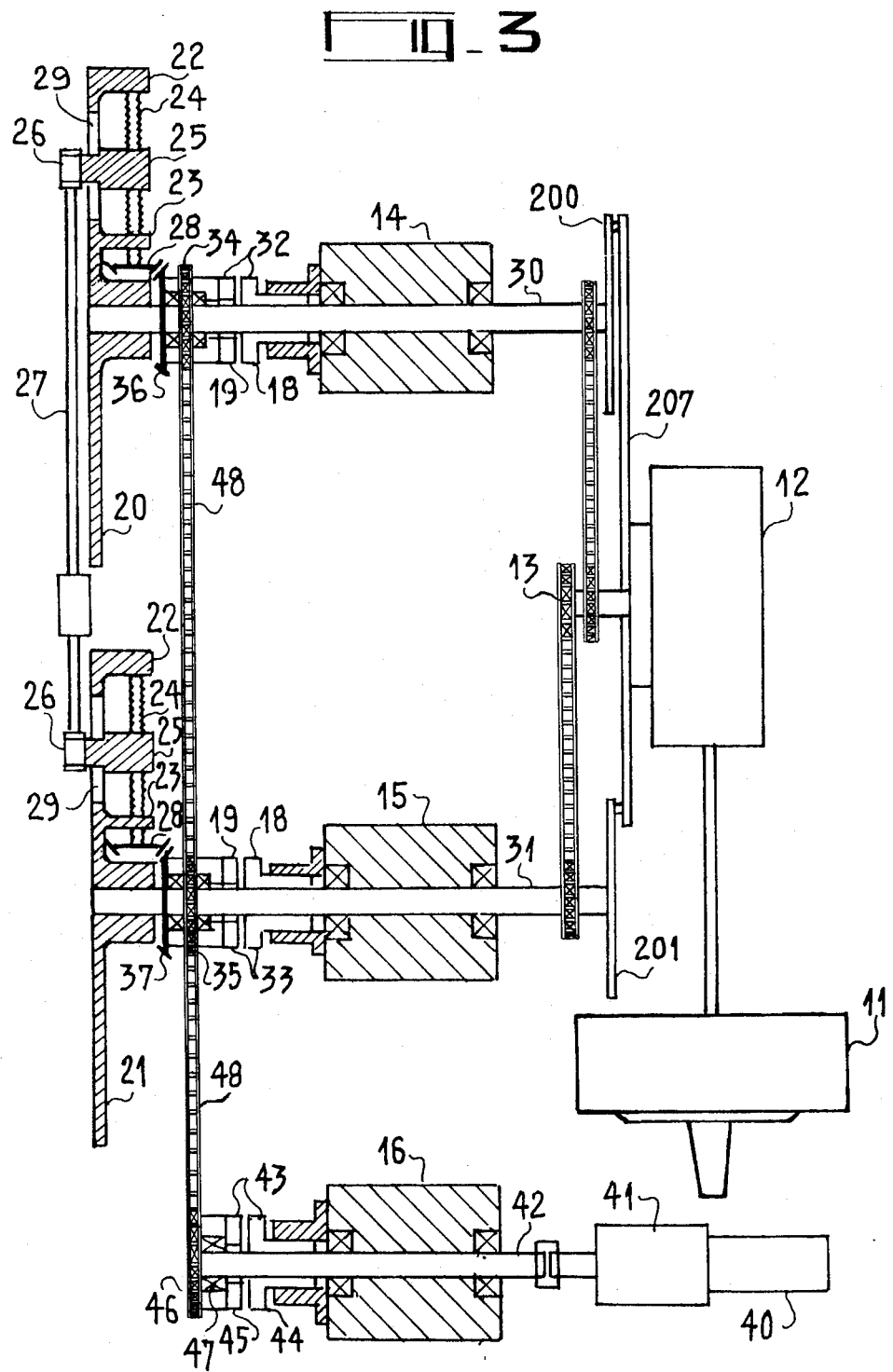
FIG. 3 is a more detailed illustration of the rectilinear scanning mechanism, partly in section.

In FIG. 3, a sectional plan view, partially exploded, of an embodiment of the rectilinear scanning mechanism has been shown.

An electric motor 11 drives a reduction gear 12 whose output shaft 13 causes two parallel shafts 30 and 31, respectively carried by the fixed bearings 14 and 15, to rotate synchronously.

Assembled on the respective shafts 30 and 31 are two electromagnetic clutches 32 and 33 whose driving sections 18 are integral with the shafts 30 and 31, and the driven sections 19 of which are each integral with a chain sprocket 34 and 35 and a bevel gear 36, 37. These assemblies (section 19 and gears) are assembled to rotate idly on the shafts 30 and 31.

Keyed to the shafts 30 and 31 there are two discs 20 and 21, each with two radial bearings 22 and 23 between which there are assembled screws or threaded shafts 24 along which nuts 25 can displace axially.

These nuts 25 carry shafts 26 parallel to shafts 30 and 31 which make up the points of attachment and articulation for the coupling link 27. The screws 24, at their tips, in the neighbourhood of the shafts 30 and 31, carry bevel gears 28 which mesh respectively with the bevel gears 36 and 37.

At the other ends of the shafts 30 and 31, two discs 200 and 201 are assembled, connected by a second coupling link 207, the angular position of the discs 200 and 201 and of the link 207, being respectively identical to those of the discs 20 and 21, and the link 27. This system is used to produce control signals and will be described in more detail making reference to FIG. 4.

In the mechanism shown in FIG. 3, the device for adjusting the amplitude of scan comprises, parallel to said first kinematic chain, a second motor 40 which drives a reduction gear 41 whose output rotates a shaft 42 carried in a third fixed bearing 16.

Assembled on the shaft 42 is an electromagnetic clutch 43 the driving section 44 of which is integral with the shaft 42 and the driven part of which 45 is integral with a chain sprocket 46.

The assembly 45 and 46 is idly mounted on the shaft 42 through a bearing 47. A chain 48 connects the sprocket 46 to the two chain sprockets 34 and 35.

To produce the rectilinear reciprocating motion, the sections 18 and 19 of the clutches 32 and 33 on the shafts 30 and 31, are engaged and the sections 44 and 45 of the clutch 43 on the shaft 42, are disengaged. The power is then supplied to the motor 11, the shafts 30 and 31 will rotate together and at the same speed, driving the discs 20 and 21 as well as the chain sprockets 34 and 35 and the bevel gears 36, 37 and 38, which then rotate synchronously (one with the discs, the other about its axis). Thus, there is no relative motion, one to the other, and the screws 24 do not rotate. The nuts 25 do not displace along the screws 24 and the link 27 performs a rectilinear reciprocating sinusoidal motion in a vertical plane.

The sprockets 34 and 35 which do rotate, through the medium of the chain 48, the sprocket 46 and the driven section 45 of the clutch 43 carried by the shaft 42, drive the assembly 45 and 46 which rotates idly on said stationary shaft 42.

It should be pointed out at this juncture that this kind of clutch mechanism, compared with the prior art type utilising screwed spindles and nuts in order to convert a rotary motion into a rectilinear motion, has the advantage that there is no reversal of the direction of rotation of the motor in order to reverse the direction of the rectilinear motion.

In order to adjust the amplitude of scan 2R, that is to say simultaneously adjust the positions of the nuts 25 on the threaded shafts 24, the friction clutches 32 and 33 are disengaged and the clutch 43 is operated. If the motor 40 is then made to rotate, with the motor 11 halted, then the shaft 42 as well as the sprocket 46 which is secured thereto by means of the clutch 43, will be made to rotate. The sprocket 46 in turn and simultaneously, through the medium of the chain 48, drives the chain sprockets 34 and 35 which then rotate idly on the halted shafts 30 and 31. The bevel gears 36 and 37 respectively integral with the chain sprockets 34 and 35, mesh with those 28 at the ends of the threaded shafts 24, causing them to rotate in order to displace the nuts 25 which are guided by slotted openings 29 formed in the discs 20 and 21, along the shafts 24 in one direction or the other, depending upon the direction of rotation of the second motor 40, so that the distance R between the axes of the discs 20 and 21 (the shafts 30 and 31) and the axes of the pivots 26 at the respective ends of the link 27, is varied. The amplitude 2R defined between the two terminal positions of the link 27 will therefore be changed.

Figure 4:
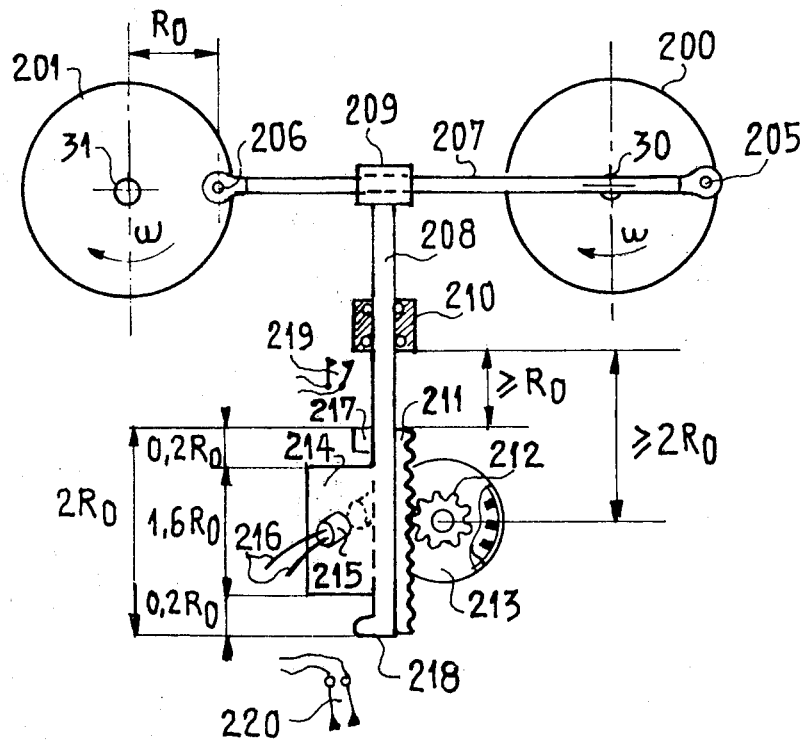
FIG. 4 illustrates the device for generating control signals as a function of the position of the source and detector assembly.

FIG. 4 illustrates a possible embodiment of the device for generating control signals as a function of the position of the source-detector assembly, these signals being required for the sampling and storage of the signals produced by the detector.

During the rectilinear scanning motion which has an amplitude of 2R (see FIGS. 2 and 3), it is required to divide up this length into n segments of equal length $d$, and to pick off just once in each of these n segments the electrical signal furnished by the radiation detector in response to the radiation emitted by a source, which radiation has passed through the object being examined. Since the amplitude 2R is variable, it is required, during a complete scanning motion, to produce $n$ signals each of which corresponds to an elementary displacement of length $d$ which is a function of R, whatever the latter's value, that is to say $d = 2R/n$.

This can be achieved if a second mechanism similar to that converting the rotational motion into a rectilinear reciprocating sinusoidal motion, described hereinbefore and illustrated in FIG. 3, is constructed in order to furnish a rectilinear reciprocating motion of amplitude $2R_o$ which is constant and which is synchronous and in phase or in phase opposition with the motion of the discs 20 and 21 and of the link 27.

To this end, at the respective free ends of the shafts 30 and 31, which are opposite to those carrying the first discs 20 and 21, two second disc 200 and 201 respectively provided around their peripheries, at distances from the shaft axes equal to $R_o$, with two pivots 205 and 206 arranged in the same angular position as the shafts 26 on the first discs. A second coupling link 207 is articulated at its respective ends, to said two pivots 205 and 206. The second link 207 carries a rod 208 in a first sleeve 209, said rod 208 being guided perpendicularly to the link 207 by means of a second sleeve 210 placed between the two discs 200 and 201 beyond a line tangential to their circumferences. The rod 208, which undergoes a displacement similar to that of the source-detector assembly driven by the first link 27 of FIG. 3, but of constant amplitude ($2R_o$), is utilised here to operate signal generators which make it possible to produce various control, sampling and address signals for the memory of the computer device (not shown).

To this end, along the free end of the rod 208, a rack 211 has been attached meshing with a gear 212 the shaft of which drives a coder or optical pulse generator 213 of conventional design. The coder 213 furnishes $q$ pulses per revolution of its shaft, by means of a rotating disc the periphery of which possesses for example $q$ opaque zones alternating with $q$ transparent zones, all the zones being of the same length, and which is arranged between a light source emitting a narrow beam, and a photoelectric detector furnishing pulses each time a transparent zone passes. In this way, squarewave signals are obtained whose periodicity is proportional to the speed of the rectilinear motion. If the rack 211 is designed in order to drive the gear 212 through $p$ revolutions for a displacement of $2R_o$, the coder 213 will supply $n = pq$ pulses with each rectilinear scan. The front or rear edges of these $n$ pulses correspond to $n$ locations disposed equidistantly along the path followed by the rod 208. These edges of the pulses will, for example, be arranged to trigger a monostable pulse generator (not shown) furnishing pulses of constant duration shorter than the minimum half-period of the squarewave signal furnished by the coder 213 at mid-travel, at the instant when the speed of displacement of the rod 208 is at a maximum. This generator delivers, on the one hand, a control signal which goes to a sampling gate (not shown), arranged downstream of the radiation detector and, on the other hand, a counting signal to a digital counter or to a shift register (not shown) used for delivering the address signal to the computer storage memory.

A second control signal defining the effective scanning periods and eliminating the time intervals located around the point of reversal of the direction of scan, in which the speed of the rectilinear motion is too low, is obtained by means of an opaque mask 214 mounted on the rod 208 and displaced between a light source (shielded by the mask) and a light detector 215. The length of the mask 214 is around 1.6 $R_o$ so that the detector 215 delivers at its output 216 a positive signal during the end of travel in one direction and the commencement of travel in the other, corresponding to about 0.2 $R_o$, that is to say 10 % of the amplitude. For the remainder of the time, that is to say 90 % of the amplitude, this constituting the effective scanning time, a negative signal is furnished by the detector 215 as the mask 214 occults the light source from the detector. The position of the mask 214 is adjustable so that the commencement of effective scanning slightly procedes or coincides with the leading edge of a pulse.

In addition, the rod 208 carries two stops 217 and 218 arranged at the ends of a zone having a length equal to $2R_o$, designed to respectively trip two switches 219 and 220 which indicate to the address system (not shown) the reversal of the direction of scan.

It should be pointed out that it is also possible to produce a sinusoidal rectilinear motion by assembling a single crank of length $R_o$ on one of the shafts 30 and 31 of the mechanism shown in FIG. 3, this crank having articulated to its free end a sleeve sliding on a rod of length $2R_o$. The two ends of the rod carry two parallel stubs, perpendicular both to the rod and to the shaft carrying the crank. These stubs, which are respectively axially guided in slides, reproduce the alternating rectilinear motion of the source-detector assembly.

FIG. 5 illustrates in a partially cut-away fashion, a front elevational view of an embodiment of the scanning device in accordance with the invention.

Figure 6:
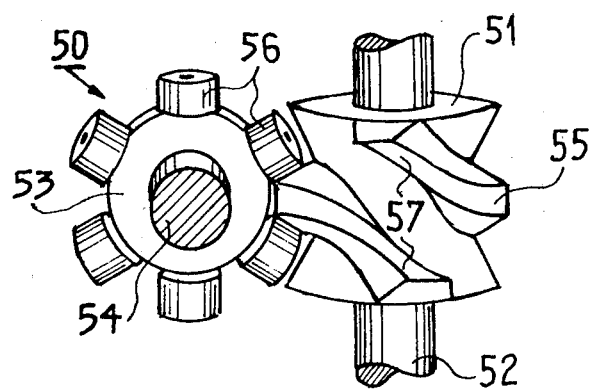
FIG. 6 schematically illustrates a conventional indexing mechanism for transforming the continuous rotary motion of the motor into an intermittent rotary motion of the support, which is to be synchronized with the rectilinear scanning motion.

The device shown in FIG. 5 comprises a fixed annular support or base 60 attached to the ground in such a manner (not shown) as to define a horizontal axis 61. The fixed annular support 60 carries an annular mobile component 62 by means of rollers (not shown) in order to enable it to rotate about the horizontal axis 61. On the annular component 62 there is integrally assembled a mounting or supporting plate 63, these two components together forming a first movable support or rotary mounting. The mounting plate 63 contains a central circular opening 64 making it possible to place any transverse section of the object or patient being examined, in the field of the radiation, and it carries the stator of the electric motor 11 controlling both the rectilinear scanning performed by the first mechanism described hereinbefore and shown in FIG. 3, and the intermittent rotation of the first movable support 62, 63, this by means of a second mechanism including a conventional indexing mechanism 50, which will be described later on and is illustrated in FIG. 6.

The motor 11, through belt transmission arrangements, first of all drives a first reduction gear 12 whose output shaft 13 is coupled, through a sprocket transmission and a first chain 65, to the shafts 30 and 31 carrying the discs 20 and 21 which constitute the double-crank system in which the two cranks are connected together by the first coupling link 27. The assembly constituted by this mechanism and the transmission arrangements, is carried by the first movable support 63. The first link 27 has a sleeve 70 slidably assembled on it, which is connected to a frame 71 of U-shaped design with two parallel legs 72 perpendicular to the link 27 and arranged at either side of the central opening 64. The two parallel legs 72 of the frame 71 are respectively longitudinally guided (perpendicularly to the link 27) by a square-section rod 73 and a system of slides 75, and they respectively carry an X-ray source the protective casing of which is marked 76, a radiation detector (not shown). The frame 71, with its parallel legs 72, thus constitutes a second movable support guided to execute a rectilinear translatory motion and driven by means of the first mechanism shown in FIG. 3.

The motor 11, also through belt transmission arrangements, drives a second reduction gear 76 whose output shaft is coupled to the input shaft 52 of the aforesaid indexing mechanism 50. The output shaft 54 of said mechanism 50 carries a chain sprocket 58 meshing with a second chain 67 which, through the medium of another sprocket 68, drives a shaft 69. The shaft 69 carries a sprocket 79 cooperating with a third chain 80 which is fixed and stretched around the external periphery of the fixed annular mounting 60. The rotation of the sprocket 79 produces displacement of the first mobile mounting 62, 63 in relation to the fixed annular mounting 60.

The transmission ratios and the respective settings of the scanning mechanism and the transmission systems linking it with the motor 11, as well as those of the system comprising the indexing mechanism 50 and the transmissions linking it to the motor 11 and to the chain 80, have been designed and set so as to cause the first mobile mounting to pivot through a given angle (for example 1°) for each half revolution of the discs 20, 21, when they are in the extreme positions of the link 27.

The first movable support furthermore carries a cam (not shown) operating two switches (not shown) carried by the fixed mounting and indicating the extreme angular positions of the first mobile mounting, which positions are located at an angle of 180° from one another.

It should be pointed out here that the fixed chain 80 can be replaced by a fixed geared ring secured to the fixed base and meshing with a gear driven by the indexing mechanism 50.

It should be noted, furthermore, that the X-ray source 76 can emit one or several parallel, collimated beams, perpendicular to the axis of rotation 61 of the first mobile mounting 62, 63. In this case, the leg 72 of the frame 71 will also carry a number of radiation detectors corresponding to the number of beams, respectively disposed in such a fashion as each to receive one of the emitted beams.

In one embodiment of the scanning device, two beams emitted by an X-ray source define two parallel planes intersecting the axis of rotation 61 at two different locations separated from one another by a given distance. In this way, with each complete cycle two transverse tomographies are obtained.

It will be clear that the frame 71 could carry several source-detector assemblies operating in the same plane, thus reducing the amplitude of scan required to cover the object being examined.

In FIG. 6, a simplified illustration of the so-called indexing mechanism 50 of FIG. 5, has been shown, this mechanism making it possible to produce intermittent pivoting of the mobile mounting upon which the source-detector assembly and the rectilinear scanning mechanisms of FIG. 3, are mounted.

The indexing mechanism 50 is an entirely mechanical system which effects conversion of a constant-speed rotational motion into an intermittent rotating motion, and one example of such a mechanism is a so-called 'Maltese cross" mechanism.

The indexing mechanism shown in FIG. 6, comprises, inside a housing (not shown), a rotating cam 51 fixed to the input shaft 52, and a roller ring or turret 53 fixed to the output shaft 54. The input shaft 52 and output shaft 54 are perpendicular to each other and located in different planes. The cam 51, which is generally concave in form, exhibits an inclined portion or rib 55, which engages between the rollers 56 disposed radially at the periphery of the turret 53. A portion of the rib 55 is ring-shaped (i.e. its axis is located in a plane perpendicular to input shaft 52) so that when the rollers 56 engage there, the turret 53 remains stationary despite rotation of the cam. The angle between the cam 51 and the inclined plane 55, at this location, is referred to as the "stop angle", "reset angle" or "dead angle".

The oblique shape of the other part 57 of the inclined portion 55 of the cam 51, produces rotation of the ring 53 through an indexing angle and at a speed, which are predetermined and respectively depend upon the length of the cam 55 and the inclination of the oblique part 57 thereof. Before one roller 56 has left one end of the inclined plane 55, another 56 has come into engagement with its other end so that continuity of motion is ensured. Thus, one revolution of the cam 51 represents a complete indexing cycle during which the ring 53 changes from one position to the next and stays there for a given time. During a complete rotation of the ring 53, this operation takes place a certain number of times, this being referred to as the "number of stops".

The indexing mechanism 50 used here is driven by the same motor 11 which drives the rectilinear scanning mechanism of FIG. 3, between the spindle of the motor 11 and the input shaft 52, as well as between the output shaft 54 and the gear 79 meshing with the ring gearing or the sprocket meshing with the fixed tensioned chain 80, reduction gear systems being arranged so that at the end of each rectilinear scanning motion, at the instant of reversal of direction of said motion, the pivoting first movable support 62 turns through a given angle (for example 1 degree), this until the mobile mounting has completed a cycle of 180°.

Of course, the invention is not limited to the embodiment described and shown which was given solely by way of example.

What is claimed is:

1. A scanning device for axial transverse tomography of the kind in which at least one beam of penetrating radiation emitted by at least one source of such a radiation and received, after passing through an object to be examined, by at least one radiation detector integrally mounted with said source, is imparted, on the one hand, a rectilinear reciprocating scanning motion in order to displace the beam perpendicular to itself in a plane and over a given distance and, on the other hand, at the time of reversal of the direction of the rectilinear scanning motion, an intermittent rotary motion about an axis perpendicular to the plane scanned by the beam, in order to make said beam pivot through a predetermined angle about said axis, said scanning device comprising a fixed support secured to the ground; a first movable support mounted on said fixed support for rotation about said axis; a first motor means mounted on said first movable support and having a shaft providing a continuous rotary motion; a fixed geared structure secured to said fixed support for engaging with a first driving gear journalled to said first movabe support; a first mechanism called an indexing mechanism, having an input shaft coupled to the shaft of said first motor means for transforming said continuous rotary motion into an intermittent rotary motion of an output shaft coupled to said first driving gear; a second movable support mounted slideably on said first movable support for rectilinear translatory motion thereon and carrying said sources and said detectors; and a second mechanism couped to said shaft of said first motor means for transforming said continuous rotary motion into a reciprocating rectilinear motion of adjustable amplitude of said second movable support relatively to said first movable support, the transmission ratios and the settings of the coupling elements between said first motor means' shaft and, on the one hand, said first driving gear through said first mechanism and, on the other hand, said second mechanism being so determined as to cause each of said intermittent rotary motions of said first movable support to coincide with each reversal of the direction of the reciprocating motion of said second movable support.

2. A scanning device as claimed in claim 1, further comprising a third mechanism coupled to said second mechanism for driving a component including an axially guided elongated portion to carry out a rectilinear reciprocating motion of constant amplitude in synchronism and in phase with the displacements of said second movable support; a first signal generator coupled to said elongated portion for generating first signals, whose periods correspond respectively to segments of equal lengths of the rectilinear trajectory of said elongated portion, said first signals controlling the periodical sampling and transmission of the respective output signals of said detectors corresponding to equidistant scanning intervals.

3. A scanning device as claimed in claim 2, further comprising a second signal generator coupled to said elongated portion for producing second signals defining effective scanning periods which exclude the intervals located to either side of the reversal in the direction of the rectilinear scanning motion.

4. A scanning device as claimed in claim 2, wherein said fixed mounting comprises a hollow fixed annular portion defining said axis of the intermittent rotary motion; wherein said first movable support carrying out said intermittent rotary motion comprises a mobile annular portion whose external periphery is rotatably assembled on the internal periphery of said fixed annular portion, said first movable support further comprising a flat portion integral with said mobile annular portion including circular central opening for allowing the passage of the object to be examined by scanning; and wherein said fixed geared structure meshing with said first driving gear is secured around the external periphery of said fixed annular portion.

5. A scanning device as claimed in claim 3, wherein said fixed mounting comprises a hollow fixed annular portion defining said axis of the intermittent rotary motion; wherein said first movable support carrying out said intermittent rotary motion comprises a mobile annular portion whose external periphery is rotatably assembled on the internal periphery of said fixed annular portion, said first movable support further comprising a flat portion integral with said mobile annular portion including circular central opening for allowing the passage of the object to be examined by scanning; and wherein said fixed geared structure meshing with said first driving gear is secured around the external periphery of said fixed annular portion.

6. A scanning device as claimed in claim 4, wherein said fixed geared structure is made up from a chain stretched around the external periphery of said fixed annular portion, said first driving gear being constituted by a sprocket-wheel.

7. A scanning device as claimed in claim 5, wherein said fixed geared structure is made up from a geared ring secured to the external periphery of said fixed annular portion coaxially therewith, said first driving gear being constituted by a pinion.

8. A scanning device as claimed in claim 4, wherein said second mechanism for providing said reciprocating rectilinear motion comprises two parallel shafts, both parallel to said axis of the intermittent rotary motion and journalled in bearings fixed to the first movable support, said two shafts being coupled to the shaft of said first motor means for being driven synchronously thereby; two first cranks of adjustable lengths respectively integral with the corresponding ends said two shafts, each of said first cranks carrying at their free ends a spindle parallel to said two shafts; a first coupling link of length equal to the center-to-center distance between said two shafts and journalled by its respectives ends on said spindles; a first sleeve assembled on said first link slideably therealong, said first sleeve being secured to said second movable support, which comprises two parallel legs disposed at either side of said central opening and respectively carrying said source and said detector; and means for guiding said second movable support along a rectilinear path perpendicular to both said first link and said axis of the intermittent rotary motion, coupled slideably to the respective parallel legs thereof.

9. A scanning device as claimed in claim 5, wherein said second mechanism for providing said reciprocating rectilinear motion comprises two parallel shafts both parallel to said axis of the intermittent rotary motion and journalled in bearings fixed to the first movable support, said two shafts being coupled to the shaft of said first motor means for being driven synchronously thereby; two first cranks of adjustable lengths respectively integral with the corresponding ends of said two shafts, each of said first cranks carrying at their free ends a spindle parallel to said two shafts; a first coupling link of length equal to the center-to-center distance between said two shafts and journalled by its respectives ends on said spindles; a first sleeve assembled on said first link slideably therealong, said first sleeve being secured to said second mobile movable support, which comprises two parallel legs disposed at either side of said central opening and respectively carrying said source and said detector; and means for guiding said second movable support along a rectilinear path perpendicular to both said first link and said axis of the intermittent rotary motion, coupled slideably of the respective parallel legs thereof.

10. A scanning device as claimed in claim 8, wherein said third mechanism comprises two second cranks of equal and fixed lengths respectively integral with said two parallel shafts at their ends opposite to the ones carrying said first cranks; a second link of length equal to the center-to-center distance between said two shafts and respectively journalled by its respective ends to the free ends of said second cranks; a second sleeve slideably mounted on said second link; a straight rod secured to said second sleeve making up said axially guided elongated portion; and a further guide means secured to said first movable support make up from a third sleeve into which said rod is inserted for sliding perpendicularly to both said second link and said axis of the intermittent rotary motion.

11. A scanning device as claimed in claim 8, wherein each of said first cranks of adjustable lengths comprises a first disc integral with one of said two parallel shafts and equipped with an elongated radial opening; two bearings arranged at the respective ends of said opening; a threaded shaft parallel to the radius of the disc rotatably carried by said bearings; a nut screwed on to the threaded shaft, arranged between the two bearings and guided for axial displacement parallel to a radius of the disc, said nut carrying said spindle journalled to one end of said first link; a first bevel gear integral with said threaded shaft disposed in proximity to one of said two parallel shafts; a second bevel gear meshing with the first one and mounted by means of bearings on one of said two parallel shafts for idly rotating thereon; a first sprocket integral with said second bevel gear; a first clutch, whose driving section is integral with one of said two parallel shafts and whose driven section is integral with said first sprocket and said second bevel gear; and wherein said scanning device further comprises a device for simultaneously adjusting said adjustable crank lengths including a motor coupled through a second clutch to a second sprocket which is coupled simultaneously by means of a second chain to said two first sprockets, whereby to synchronously control the rotation of said two threaded shafts by means of said bevel gears, while said two parallel shafts are halted and said first clutches disengaged.

* * * * *